United States Patent [19]
Adair

[11] 4,205,678
[45] Jun. 3, 1980

[54] METHOD AND APPARATUS FOR ATTACHING AN OSTOMY BAG

[76] Inventor: Edwin L. Adair, 7850 Platte Canyon Rd., Littleton, Colo. 80120

[21] Appl. No.: 685,440

[22] Filed: May 11, 1976

[51] Int. Cl.² .............................................. A61F 5/44
[52] U.S. Cl. ................................................... 128/283
[58] Field of Search ................ 128/1 R, 1.3, 283, 284, 128/286, 287, 290 R, 346, 347, 348, 349 R, 350 R, DIG. 25, 217; 3/1; 32/2

[56] References Cited
U.S. PATENT DOCUMENTS

| | | | |
|---|---|---|---|
| 2,513,014 | 6/1950 | Fields | 128/217 |
| 3,565,073 | 2/1971 | Giesy | 128/283 |
| 3,952,726 | 4/1976 | Hennis et al. | 128/283 |
| 3,991,743 | 11/1976 | Bucalo | 128/1 R |

FOREIGN PATENT DOCUMENTS 2363563  6/1975  Fed. Rep. of Germany ........... 128/283

Primary Examiner—Robert W. Michell
Assistant Examiner—C. F. Rosenbaum
Attorney, Agent, or Firm—Sheridan, Ross, Fields, & McIntosh

[57] ABSTRACT

Ostomy bag securing apparatus, and method of applying same, characterized by implanting a plurality of small powerful permanent bar magnets through skin punctures to positions beneath the skin and surrounding a stoma, without surgical cutting of the skin, and applying a magnetically permeable collar, having a bag removeably affixed thereto, on the outer surface of the skin, concentric with the magnets. Alternatively, the implanted bars may be magnetically permeable, but not permanently magnetized, and permanently magnetized bars disposed on the collar which latter may be formed of non-magnetic material.

10 Claims, 7 Drawing Figures 4,205,678

METHOD AND APPARATUS FOR ATTACHING AN OSTOMY BAG

BACKGROUND OF THE INVENTION

During certain surgical operations it becomes necessary to reorient certain body waste ducts to locations other than their normal terminal locations in the body. For example, a colon or ureter may be reoriented to terminate at the surface of the abdomen and to which a bag may be attached for communicating with the end of the duct, the bag being removeable to dispose of waste matter which is discharged thereto. Various securing means to the skin, such as adhesive, straps, and the like, have heretofore been employed with variable success. A recent development which obviates the use of such securing means is exemplified by the patent to Giesy, U.S. Pat. No. 3,565,073 in which a magnetic ring is embedded beneath the skin and surrounding the terminal end of the duct, known as a stoma, which magnetically attracts a magnetically permeable ring which lies on the surface of the skin, a bag being removeably attached to such ring.

While the device just referred to, and which is probably the most closely related to the present invention, has various advantages over attaching means previously employed, it is disadvantageous, inter alia, in that the magnetic ring must be implanted beneath the skin by surgical cutting of the skin and subsequent healing entailed therewith.

SUMMARY OF THE INVENTION

Method and apparatus for removeably securing a waste matter or ostomy bag to the skin of a user at a locus surrounding a stoma, characterized by embedding a plurality of spaced small powerful permanent bar magnets beneath the skin in a ring configuration surrounding the stoma without surgical incision of the skin. Each magnet is embedded by puncturing through the skin with a trocar including a needle and surrounding sheath, removing the needle, inserting a magnet in the sheath, pushing it to the implanted end thereof, removing the sheath to embed the magnet below the skin, and thence permitting the skin to resiliently close the needle puncture. A collar of magnetically permeable material having a removeable bag is disposed on the external surface of the skin, concentric with the ring of magnets which latter attract the collar into sealing engagement with the surface of the skin.

In an alternative form of the invention, the bars inserted beneath the skin may be magnetically permeable, but not permanent magnets, and the permanent bar magnets may be carried by the collar, preferably removeable, so that they may be sequentially removed, gradually decreasing the magnetic attraction between the embedded bars and the collar.

Cobalt-samarium magnets, relatively recently developed, which have considerably greater flux density than previously known permanent magnets, are preferably employed in both embodiments.

DETAILED DESCRIPTION OF THE PREFERRED EMBODIMENTS

Figure 1:
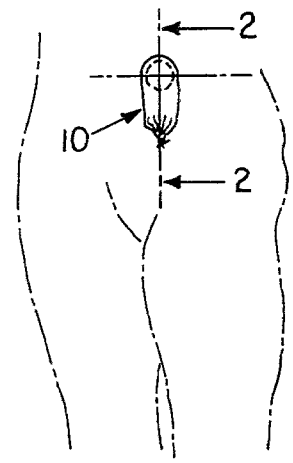
FIG. 1 depicts, to greatly reduced scale, an ostomy bag secured to the abdomen of a patient.
Figure 2:
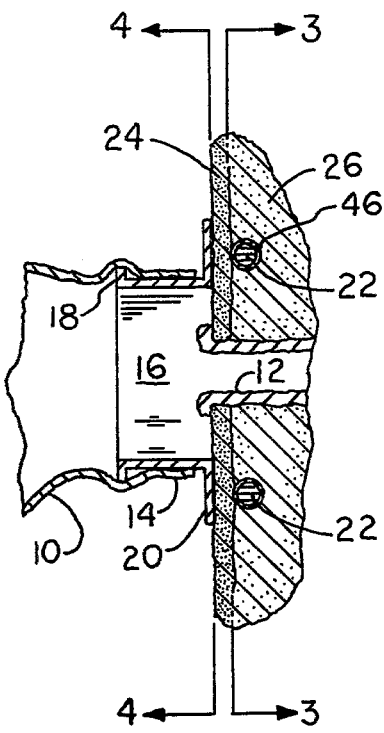
FIG. 2 is an enlarged section taken on line 2—2, FIG. 1.

Referring now to the drawing, FIG. 1 illustrates an exemplary portion of the human body to which an ostomy bag or waste matter receptacle 10 is attached, which receives waste matter discharged through stoma 12 (FIG. 2), which, for purposes of illustration, may be considered as the terminal end of a colon after surgical reorientation thereof to the surface of the abdomen, all as is conventional in the patent referred to. As best shown in FIG. 2, the resilient mouth 14 of the bag removably engages a collar 16, having flanges 18, 20 at ends thereof. In the first form of the invention to be subsequently described, the collar may be formed of ferrous material, such as soft steel, suitably plated or coated (not shown) to render it inert and compatible with skin, the collar being permeable to magnetic flux, but not a permanent magnet when removed from a magnetic field. Alternatively the collar may be non-magnetic, such as plastic with a magnetic ring secured to flange 20 (not shown). As will be understood from the foregoing examples, the collar may be suitably proportioned for attachment around ileostomies, urostomies and ureterostomies and other body openings wherein a body duct has been surgically reoriented from its normal position to a desired terminal locus at the surface of the skin.

As hereinafter employed, "permanent" magnet or "magnetized" will be understood to be synonymous, "magnetic" as magnetically permeable to magnetic flux but not magnetized when removed from such flux, and "non-magnetic" as not susceptible to being magnetized.

The principal novelty over the patent referred to will now be described. In the patent, a magnetized ring is implanted beneath the skin, which, as alluded to, requires surgical incising, suturing, and healing. In the present invention, a plurality of cylindrical permanent bar magnets 22 are implanted beneath skin 24, overlying fascia 26, which exert the attraction force in the patent referred to, these being disposed concentric about stoma 12. While eight are shown as exemplary, any number may be employed to produce the requisite magnetic attractive force to maintain flange 20 in sealing engagement with the outer surface of the skin. To obtain the requisite magnetic force with a minimum number of magnets, the magnets are preferably of the recently developed type containing cobalt and samarium, this material being susceptible to permanent magnetization with a flux density considerably higher than magnets heretofore known such as those known as "Alnico" permanent magnets.

Figure 5:
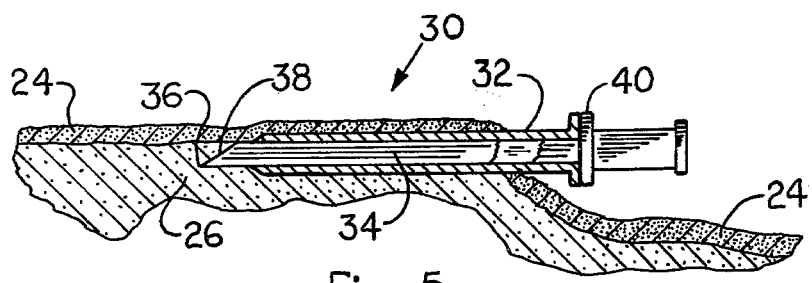
FIGS. 5 and 5A illustrate apparatus and method for implanting bars beneath the skin.
Figure 5A:
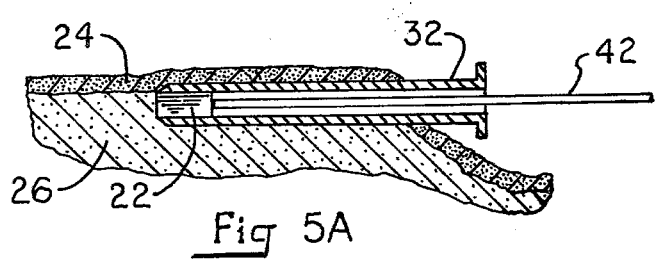

A method and apparatus for implanting the magnets without surgical incision by scalpel or the like and suturing the incision, will now be described. FIG. 5 illustrates to trochar 30 comprising a tubular sheath 32, the needle 34 having a sharp puncturing point 36 which may be formed in any desired manner, such as by grinding a flat 38 on the needle. The needle may also be provided with a shoulder or stop 40 so that when the needle is inserted beneath the skin, the sheath moves therewith. As illustrated, the needle and sheath have been inserted beneath skin 24, substantially parallel thereto and above tissue or fascia 26 therebelow. The needle is then withdrawn from the sheath (FIG. 5A) and a cylindrical magnet 22 is inserted in the now open outer end of the sheath and slid through same with a rod or stylet 42 to the implanted end thereof. It is then retained in such position by the stylet and the sheath is withdrawn, thus implanting the magnet beneath the skin in the position formerly occupied by the end of the sheath, permitting the skin to close to substantially the diameter of the needle puncture, which, like a hypodermic needle puncture, permits rapid blood coagulation and healing of the puncture.

The advantages of inserting a magnet through a skin puncture, as distinguished from a scalpel incision, may be better understood from that which is to follow: when an elongated incision is made through skin by a scalpel, the skin spreads apart, the major spread being between the ends of the incision. In the absence of closing the incision by sutures or appropriate bandaging, the space between the spread skin must fill with new growth tissue, leaving scar tissue. If sutured, of course, the scar tissue is a minimum, leaving only a line, which in some cases, is invisible or substantially so. With a needle puncture, there is slight severing of the skin, particularly if the needle is ground with a flat end as shown, the edge surrounding such flat serving as a cutting edge. When the needle has passed through the skin the hole therein is now the diameter of the needle. The tapered end of sheath 32 now enters such hole and temporarily expands the skin to its larger diameter, but without further cutting of the skin. When the sheath is removed, the resilience of the surrounding skin closes it back to the needle diameter which, of course, is so small that it requires no suture, quickly closes by blood coagulation, and heals rapidly in the same manner as a hypodermic puncture, that of a needle employed for extracting a blood sample from a vein, or a trochar for implanting a tube within a blood vessel.

Figure 2A:
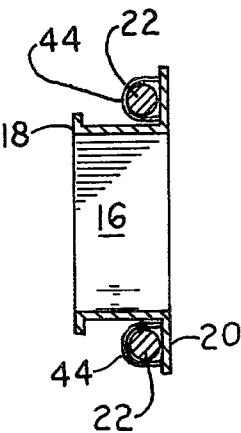
FIG. 2A is an alternative form of the construction illustrated in FIG. 2.
Figure 3:
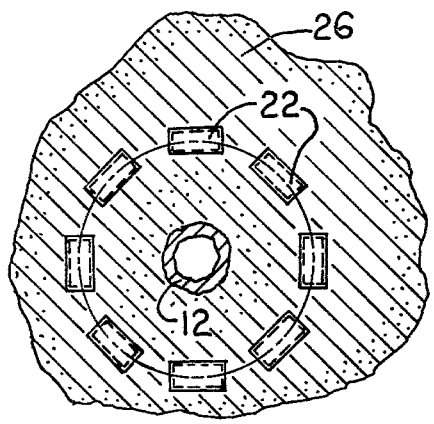
FIG. 3 is a section taken on line 3—3, FIG. 2.
Figure 4:
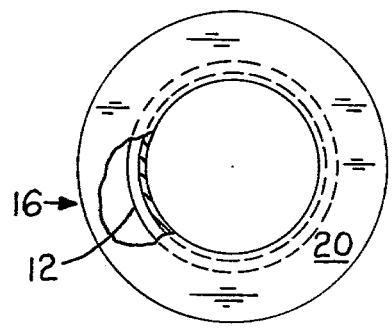
FIG. 4 is a section taken on line 4—4, FIG. 2, a portion being broken away.

In the construction so far described, the ferrous collar will normally remain on the user and the bag emptied from time to time, either by opening its lower closed end, as shown in the patent referred to, or removing it from the collar for disposal and replacement. It may be desirable to remove the collar on occasion, however, for sanitary or medical attention to the zone covered thereby. Since the magnetic attraction between the embedded magnets and the collar may be considerable, some difficulty may be experienced in overcoming this force by pulling the collar away from the skin. If such removal is anticipated at frequent intervals an alternative form of the invention may be employed to more readily facilitate removal of the collar. In this construction, the embedding procedure is identical but the embedded bars may be magnetic rather than magnetized material. The permanent magnets, as shown in FIG. 2A, are then removably disposed on the collar, such as with clips 44 or the like, these, of course, being in alignment with the embedded magnetic bars. When it is desired to remove the collar, the magnetized bars are sequentially removed from the collar, thus gradually reducing the magnetic force until none exists, after which the collar may be readily removed from the skin.

The implanted bars, whether magnetized or magnetic, are preferably encapsulated within a thin coating 46 which is inert, non-toxic, and otherwise compatible with body chemistry.

What is claimed is:

1. An ostomy apparatus of the type having first means comprising an annular collar with an end face adapted to lie on the surface of the skin of a human body and surrounding a stoma having a terminal end at the surface of the skin, and second means adapted to be implanted beneath the skin, spaced outwardly from and around the stoma in a locus juxtaposed to said end face, one of said means being magnetized and the other being magnetic, whereby the two means are attracted toward each other to thereby maintain said end face in facial sealing engagement with the outer surface of the skin, the improvements, in combination, comprising:
   (a) said second means comprising a plurality of elongated bars disposed in spaced relationship in a ring-like configuration, each bar being disposed within a separate needle puncture through the skin, and without other incision thereof, whereby after insertion, healing of the skin is limited to the zones of the separate punctures.

2. Apparatus in accordance with claim 1 wherein the first means is magnetic and the second means are magnetized.

3. Apparatus in accordance with claim 1 wherein the first means includes magnetized means and the second means are magnetic.

4. Apparatus in accordance with claim 2 wherein each of the second means is encapsulated in material which is inert, non-toxic, and compatible with the human body.

5. Apparatus in accordance with claim 3 wherein said magnetized means comprises a plurality of magnetized bars removably secured to the first means, whereby they may be removed therefrom to eliminate the magnetic attraction between the two means.

6. Method of effecting securement of ostomy apparatus to the surface of the skin of a human body, the apparatus being of the type having first means comprising an annular collar with an end face adapted to lie on the skin of the human body, and surrounding a stoma having a terminal end at the surface of the skin, and second means implanted beneath the skin in a locus juxtaposed to said end face, one of said means being magnetized and the other being magnetic, whereby the two means are attracted toward each other to thereby maintain said end face in facial sealing engagement with the outer surface of the skin, said second means comprising a plurality of bars disposed in spaced relationship in a ring-like configuration, said method comprising the steps of:
   (a) forming a needle puncture through the skin for each bar, and without other incision thereof,
   (b) inserting a bar into each needle puncture to its final position of installation beneath the skin, and
   (c) permitting each needle puncture to heal.

7. Method in accordance with claim 6 including the steps of enlarging each needle puncture with a hollow sheath surrounding the needle, removing the needle from the sheath, inserting a bar through the sheath to the inner end thereof, and removing the sheath, to permit the surrounding skin to contract to a size substantially the size of the needle.

8. Method in accordance with claim 7 wherein each bar is magnetized.

9. Method in accordance with claim 7 wherein each bar is magnetic.

10. Method in accordance with claim 9 including the steps of applying a plurality of magnetized bars to the collar to render same attractive toward the imbedded magnetic bars, and removing same therefrom when it is desired to remove the collar from the skin.

* * * * *